United States Patent [19]
Horwell et al.

[11] Patent Number: 5,550,126
[45] Date of Patent: Aug. 27, 1996

[54] CENTRAL CHOLECYSTOKININ ANTAGONISTS HAVING PHARMACEUTICAL ACTIVITY

[75] Inventors: David C. Horwell, Foxton; John Hughes, Swaffman Prior; Geoff N. Woodruff, Dassels, all of England

[73] Assignee: Merck Sharp and Dohme Limited, Hoddesdon, England

[21] Appl. No.: 380,467

[22] Filed: Jan. 30, 1995

Related U.S. Application Data

[63] Continuation of Ser. No. 286,715, Aug. 5, 1994, abandoned, which is a continuation of Ser. No. 210,251, Mar. 18, 1994, abandoned, which is a continuation of Ser. No. 96,749, Jul. 23, 1993, abandoned, which is a continuation of Ser. No. 800,861, Oct. 24, 1991, abandoned, which is a continuation of Ser. No. 421,896, Oct. 16, 1989, abandoned, which is a continuation-in-part of Ser. No. 389,665, Aug. 4, 1989, abandoned.

[51] Int. Cl.$^6$ .................. A61K 31/195; A61K 31/445; A61K 31/535
[52] U.S. Cl. .................. 514/237.5; 514/221; 514/330; 514/563
[58] Field of Search .................. 514/237.5, 330, 514/563

[56] References Cited

U.S. PATENT DOCUMENTS

| | | | |
|---|---|---|---|
| 4,769,389 | 9/1988 | Makovec et al. | 514/563 |
| 4,791,215 | 12/1988 | Rovati et al. | 558/415 |
| 4,820,834 | 4/1989 | Evans et al. | 540/504 |
| 5,004,741 | 4/1991 | Evans et al. | 514/221 |
| 5,153,191 | 10/1992 | Woodruff | 514/221 |
| 5,391,574 | 2/1995 | Makovec et al. | 514/563 |

FOREIGN PATENT DOCUMENTS

| | | | |
|---|---|---|---|
| 167919 | 1/1986 | European Pat. Off. | |
| 0411668 | 2/1991 | European Pat. Off. | A61K 31/55 |

OTHER PUBLICATIONS

*Drug Evaluations*, 6th Ed. (1986), Amer. Medical Assn., pp. 111, 113 and 299.
The Merck Index, 11th Ed., Merck & Co., Inc., pp. 383, 472, 594, 1030 (1989).
Bradwejn, J. et al., "Cholecystokinin Tetrapeptide Induces Panic Attacks Identical To Spontaneous Panic Attacks in Patients Suffering from Panic Disorder", Soc. Neurosci. Abstr., vol. 14(1), p. 291 (1988).
de Montigny, C., "Anxiety and Panic Attacks Induced By The Tetrapeptide Cholecystokinin in Healthy Volunteers", Soc. Neurosci. Abstr., vol. 14(1), p. 291 (1988).
Bradwejn, J. and de Montigny, C., "Benzodiazepines antagonize cholecystokinin–induced activation of rat hippocampal neurones", Nature, vol. 312, pp. 363–364 (1984).
de Montigny, C., "Cholecystokinin Tetrapeptide Induces Panic–like Attacks in Healthy Volunteers", Arch. Gen. Psychiatry, vol. 46, pp. 511–517 (1989).
Dourish, C. T. et al., "Enhancement of morphine analgesia and prevention of morphine tolerance in the art by the cholecystokinin antagonist L–364,718", Eur. Jour. Pharm., vol. 147, No. 3, pp. 469–472 (1988).
O'Neill, M. F. et al., "Morphine Induced Analgesia in the Rat Pressure Test is Blocked by CCK and Enhanced by the CCK Antagonist MK–329", Neuropharmacology, vol. 28, No. 3, pp. 243–247 (1989).
Chang, R. S. L. and Lotti, V. J., "Biochemical and pharmacological characterization of an extremely potent and selective nonpeptide cholecystokinin antagonist", Proc. Natl. Acad. Sci., vol. 83, pp. 4923–4926 (1986).
Bouthillier A. and De Montigny, C., "Long–term benzodiazepine treatment reduces neuronal responsiveness to cholecystokinin: an electrophysiological study in the rat", Eur. Jour. Pharm., vol. 151, No. 1, pp. 135–138 (1988).
Schick, et al. *Regulatory Peptides*, 14:277–291, 1986.
Hill, et al. *Neuropharmacology*, 26:289–300, 1987.
MacVicar, et al. *Brain Research*, 406:130–135, 1987.
Roberts, et al. *Brain Research*, 288, 199–211, 1983.
Totterdell et al. *Neuroscience* 19, 181–192, 1986.
Weiss, et al. *Pharm., Biochem. and Behaviour*, 30, 309–317, 1988.
Schneider et al. *Peptides* 4, 749–753, 1983.
Konturek *Gastrointestinal Hormones* 23 529–564, 1980.
Johnson ibid. 507–527.
Singh et al. *Cancer Research*, 46, 1612, 1986.
Smith *Gastroenterology* 95:1541, 1988.
Dockray *Br. Med Bull.* 38 No. 3:253–258, 1982.
Morley *Life Sciences* 27:355–368, 1980.
"CCK in the Nervous System," Belleroche et al, Chichester, England, 110–127, 1984.
Rehfeld et al *J. Neurochem.* 32:1339–1341, 1979.
Della–Fera et a. *Science* 206:471–473, 1979.
Demeulemeester et al *J. Neuroscience* 8:988–1000, 1988.
Harvey *The Pharmacological Basis of Therapeutics*, (7th ed.) 1985, 339–371, MacMillan.
Wall Street Journal, "Merck Advances in Drug Research to Treat Obesity", Sep. 29, 1989 p. B–4.
Mutt, *Gastrointestinal Hormones*, Ch. 7, pp. 169–221, Cholecystokinin: Isolation, structure and functions, (1980).
*Gastrointestinal Hormones*, Fl. Stadil, "Gastrinomas," 1980, pp. 729–739.

Primary Examiner—Philip I. Datlow
Attorney, Agent, or Firm—Francis P. Bigley; Mark R. Daniel

[57] ABSTRACT

Pharmaceutical compositions and methods of using CCK-ligands D,L-glutamic acid and D,L-aspartic acid as antipsychotic, antianxiety, and agents useful in treatment or prevention of withdrawal symptoms caused by withdrawal of chronic or long term use of diazepam, alcohol, cocaine or nicotine and antianxiety agents are described.

4 Claims, 2 Drawing Sheets

% TIME IN BLACK

LATENCY W → B

CENTRAL CHOLECYSTOKININ ANTAGONISTS HAVING PHARMACEUTICAL ACTIVITY

This is a continuation of application Ser. No. 08/286,715 filed on Aug. 5, 1994, now abandoned, which is a continuation of application Ser. No. 08/096,749 filed on Jul. 23, 1993, now abandoned, which is a continuation of application Ser. No. 07/421,896, filed Oct. 16, 1989, now abandoned which which is a continuation of application Ser. No. 07/800,861 filed on Oct. 24, 1991, now abandoned, which is a continuation of application Ser. No. 08/210,251 filed on Mar. 18, 1994, now abandoned which is a continuation-in-part of application Ser. No. 07/389,665 filed Aug. 4, 1989 now abandoned.

BACKGROUND OF THE INVENTION

Agents acting at central cholecystokinin (CCK) receptors induce satiety (Schick, Yaksh and Go, *Regulatory Peptides* 14:277–291, 1986. They are also expected to act as anlagesics (Hill, Hughes and Pittaway, *Neuropharmacology* 26:289–300, 1987, and as anticonvulsants (MacVicar, Kerrin and Davison, *Brain Research*, 406:130–135, 1987.

Reduced levels of CCK-peptides have been found in the brains of schizophrenic patients compared with controls (Roberts, Ferrier, Lee, Crow, Johnstone, Owens, Bacarese-Hamilton, McGregor, O'Shaughnessey, Polak and Bloom. *Brain Research* 288, 199–211, 1983). It has been proposed that changes in the activity of CCK neurones projecting to the nucleus accumbens may play a role in schizophrenic processes by influencing dopaminergic function (Totterdell and Smith, *Neuroscience* 19, 181–192, 1986). This is consistent with numerous reports that CCK peptides modulate dopaminergic function in the basal ganglia and particularly the nucleus accumbens (Weiss, Tanzer, and Ettenberg, *Pharmacology, Biochemistry and Behaviour* 30, 309–317, 1988; Schneider, Allpert and Iverson, *Peptides* 4, 749–753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, *Gastrointestinal Hormones*, Ch. 23, pp 529–564, 1980, ed. G. B. J. Glass, Raven Press, N.Y.). Antagonists of the CCK-8 receptor would also be expected to be antagonists at the stomach gastrin receptor and thus be of value for conditions involving excessive acid secretion.

CCK and gastrin peptides have trophic effects on the pancreas and various tissues of the gastrointestinal tract (Johnson, ibid., pp 507–527), actions which are associated with increased DNA and RNA synthesis. Moreover, gastrin secreting cells are associated with certain gastrointestinal tumors as in the Zollinger-Ellison syndrome (Stadil, ibid., pp 279–739), and some colorectal tumors may also be gastrin/CCK dependent (Singh, Walker, Townsend and Thompson, *Cancer Research*, 46, 1612 (1986), and Smith, J. P., *Gastroenterology*, 95:1541 (1988)). Antagonists of CCK/gastrin receptors could therefore be of therapeutic value as antitumor agents.

The cholecystokinin peptides are widely distributed in various organs of the body including the gastrointestinal tract, endocrine glands, and the nerves of the peripheral and central nervous systems. Various biologically active forms have been identified including a 33-amino acid hormone and various carboxy-terminus fragments of this peptide (e.g., the octapeptide CCK26-33 and the tetrapeptide CCK30-33). (G. J. Dockray, *Br. Med. Bull.,* 38 (No. 3):253–258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. ("Cholecystokinin: Isolation, Structure and Functions," G. B. J. Glass, Ed., Raven Press, New York, 1980, pp 169–221; J. E. Morley, *Life Sciences* 27:355–368, 1980; "Cholecystokinin in the Nervous System," J. de Belleroche and G. J. Dockray, Ed., Ellis Horwood, Chichester, England, 1984, pp 110–127).

The high concentrations of CCK peptides in many brain areas also indicate major brain functions for these peptides (G. J. Dockray, *Br. Med. Bull.,* 38 (No. 3):253–258, 1982). The most abundant form of brain CCK found in CCK26-33, although small quantities of CCK30-33 exist (Rehfeld and Gotterman, *J. Neurochem.,* 32:1339–1341, 1979). The role of central nervous system CCK is not known with certainty, but it has been implicated in the control of feeding (Della-Fera and Baile, *Science* 206:471–473, 1979).

CCK is known to be present in some cortical interneurones which also contain gamma-aminobutyric acid (GABA) (H. Demeulemeester, et al, *J Neuroscience* 8:988–1000, 1988). Agents that modify GABA action may have utility as anxiolytic or hypnotic agents (S. C. Harvey, The *Pharmacological Basic of Therapeutics* (7th ed.) 1985, pp 339–371, MacMillan). Thus, agents which modify CCK action may have parallel anxiolytic or hypnotic activities.

It has now been found that CCK-B ligands are useful as antipsychotic and as antianxiety agents. This includes all CCK-B ligands. CCK-B antagonists have now been shown to be agents useful in the treatment of withdrawal from drugs and alcohol. Although some ligands are CCK-A selective they do have some CCK-B activity as well and therefore are included also. Mixed CCK A/B ligands are also included.

The present invention is related to pharmaceutical compositions and methods of treating psychoses and/or anxiety and the withdrawal response caused by chronic treatment or abuse followed by withdrawal of drugs or alcohol using CCK-ligands and pharmaceutically acceptable salts thereof. The compounds and methods of preparing them are found in U.S. Pat. Nos. 4,791,215 and 4,820,834 and European Application 167,919. These documents are incorporated herein by reference.

The uses disclosed are gastric acid secretion disorders, gastrointestinal motility, pancreatic secretions, dopaminergic functions, analgesics, psychic disturbances, anorexia, weight increases in farm animals, and pathological cellular growth such as tumors.

SUMMARY AND DETAILED DESCRIPTION OF THE INVENTION

Figure 1A:
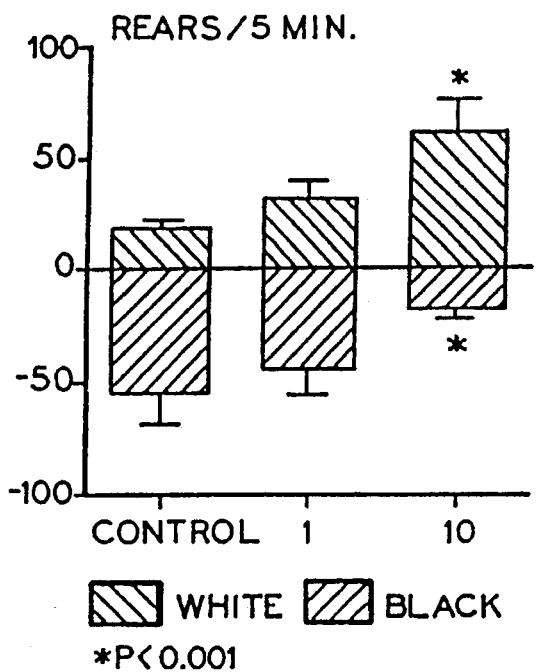
FIG. 1A. This figure depicts the relative level of rearing observed during 5 minutes in both a black and white compartment for a control group and following administration of L-365,260. The horizontal axis shows the dosage in mg/kg and the vertical axis indicates the number of rears per five minutes, as well as the number which occur in either the light part of the box which is designated as white or the number which occur in the dark or black part of the box. The number of rears which occurred in the light part of the box is indicated in the area above zero while the number of rears which occurred in the dark part of the box is indicated in the area below zero.
Figure 1B:
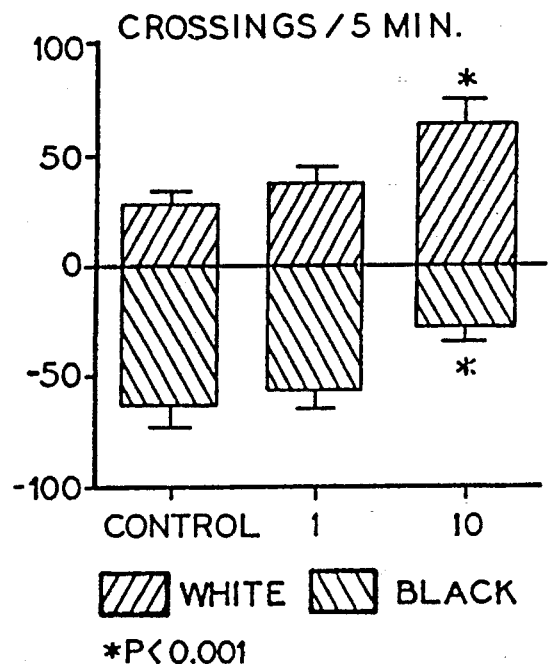
FIG. 1B. This figure depicts the relative line crossing activity during 5 minutes in a black and white compartment for a control group and for animals which have received L-365,260 in mg/kg. The horizontal axis shows the dosage in mg/kg. The vertical axis shows the number of times the rats crossed from one area to an other.

The present invention relates to a pharmaceutical composition useful in the treatment of psychoses and/or anxiety. The present invention further relates to a pharmaceutical composition useful for the treatment of withdrawal symptoms, withdrawal from drugs or alcohol. The composition comprises a therapeutically effective amount of at least one of the following CCK-antagonists or a pharmaceutically acceptable salt thereof in combination with a pharmaceutically acceptable carrier:

pharmaceutically active derivatives of D,L-glutamic acid and D,L-aspartic acid of formulae:

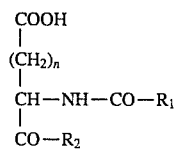

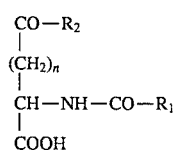

wherein n is 1 or 2

$R_1$ is a phenyl group mono-, di, or tri-substituted with linear or branched $C_1$-$C_4$ alkyl groups, which may be the same or different, or with halogens, with a cyano group or with a trifluoromethyl group;

$R_2$ is selected from the group consisting of morpholino, piperidino and amino with one or two linear, branched or cyclic alkyl group substituents containing from 1 to 8 carbon atoms which may be the same or different; of

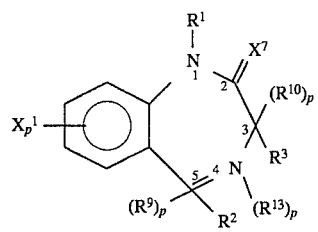

wherein $R^1$ is H, $C_1$-$C_6$ linear or branched alkyl, loweralkenyl, lower alkynyl, —$X^{12}COOR^6$, —$x^{11}$cycloloweralkyl, —$X^{12}NR^4R^5$, $X^{12}CONR^4R^5$, —$X^{12}CN$, or —$X^{11}CX_3^{10}$;

$R^2$ is H, loweralkyl, substituted or unsubstituted phenyl (wherein the substituents may be 1 or 2 of halo, loweralkyl, loweralkoxy, loweralkylthio, carboxyl, carboxyloweralkyl, nitro, —$CF_3$, or hydroxy), 2-, 3-, 4-pyridyl,

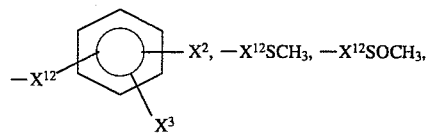

—$X^{12}SO_2CH_3$, or —$X^{12}COOR^6$;

$R^3$ is —$X^{11}R^7$, —$X^{11}CHR^7$, —$X^{11}$—C(OH)—$R^7$, —$X^{11}CR^7$,
                                    |
                                    $R_a^7$

—$X^{11}NR^{18}(CH_2)_qR^7$, —$X^{11}NR^{18}CHCOOR^6$, —$X^{11}X^9C(X^{11})R^7$,
                              |
                              $(CH_2)_q$
                              |
                              $R^7$

—$X^{11}CX^9X^{11}R^7$, —$NH(CH_2)_{2-3}NHR^7$, —$NH(CH_2)_{2-3}NHCOR^7$,

—$X^{11}X^9CCHCH_2R^7$, —$X^{11}X^9CX_a^9(X^{11})R^7$,
                          |
                          $NHCOOR^{14}$

—$X^{11}X^9C$—CH—$CH_2R^7$, —$X^{11}X^9C(CH_2)_qX_a^9$—
         |        |
         O        $NH_2$

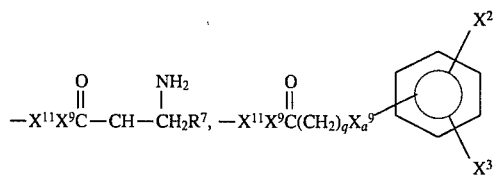

—$X^{11}NR^{18}SO_2(CH_2)_qR^7$ or =C—$R_7$
                                  |
                                  H wherein $R_4$ and $R_5$ are independently $R^6$ or in combination with the N of the $NR^4R^5$ group form an unsubstituted or mono or disubstituted, saturated or unsaturated, 4–7 membered heterocyclic ring or benzofused 4–7 membered heterocyclic ring, or said heterocyclic ring or said benzofused heterocyclic ring which further comprises a second heteroatom selected from O and $NCH_3$ and the substituents(s) is/are independently selected from $C_{1-4}$ alkyl;

$R^6$ is H, loweralkyl, cycloloweralkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or CF₃;

R₇ and R_a⁷ are independently α- or β-naphthyl, substituted or unsubstituted phenyl (wherein the substituents may be 1 or 2 of halo —NO₂, —OH, —X¹¹NR⁴R⁵, loweralkyl, CF₃, CN, SCF₃, C≡CH, CH₂SCF₃,

OCHF₂, SH, SPh, PO₃H-loweralkoxy, or loweralkylthio, COOH), 2-, 3-, 4-pyridyl

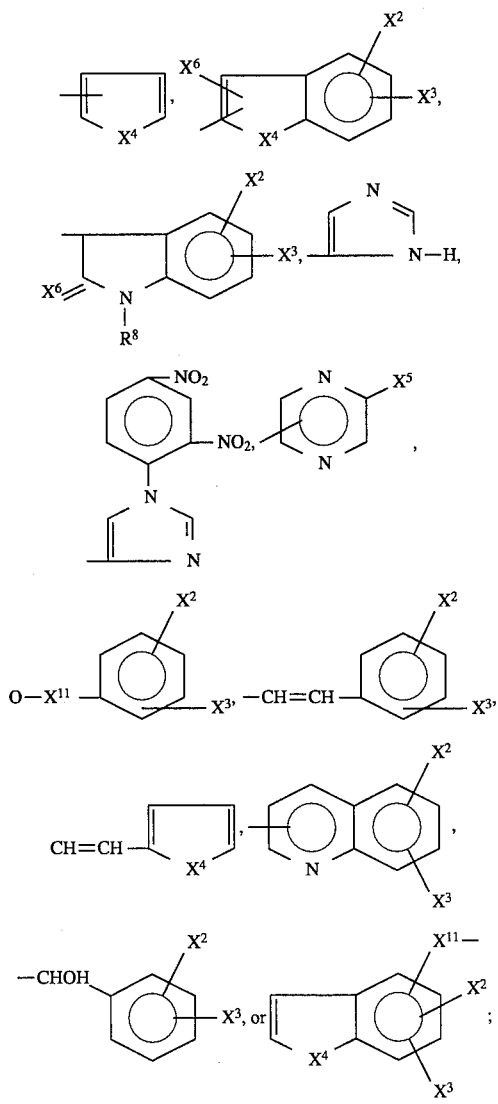

R⁸ is H, loweralkyl, cycloloweralkyl, —X¹²CONH₂, —X¹²COOR⁶, —X¹²-cycloloweralkyl, —X¹²NR⁴R⁵,

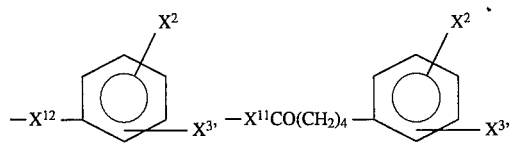

-continued

, or 

R⁹ and R¹⁰ are independently H, —OH, or —CH₃;
R¹¹ and R¹² are independently loweralkyl or cycloloweralkyl;
R¹³ is H, loweralkyl, acyl, O, or cycloloweralkyl;
R¹⁴ is loweralkyl or phenylloweralkyl;
R¹⁵ is H, loweralkyl,

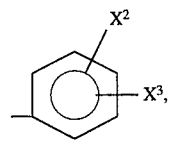

or —NH₂;
R¹⁸ is H, loweralkyl, or acyl;
p is 0 when its adjacent═is unsaturated and 1 when its adjacent═is saturated except that when R¹³ is O, p=1 and═is unsaturated;
q is 0–4;
r is 1 or 2;
X¹ is H, —NO₂, CF₃, CN, OH, loweralkyl, halo, loweralkylthio, loweralkoxy, —X¹¹COOR⁶, or —X¹¹NR⁴R⁵—;
X² and X³ are independently H, —OH, —NO², halo, loweralkylthio, loweralkyl, or loweralkoxy;
X⁴ is S, O, CH₂, or NR¹⁸ or NR⁸;
X⁵ is H, CF₃, CN, —COOR⁶, No₂, or halo;
X⁶ is O or HH;
X⁷ is O, S, HH, or NR¹⁵;
X⁸ is H, loweralkyl;
X⁹ and X_a⁹ are independently NR¹⁸ or O;
X¹⁰ is F, Cl, or Br;
X¹¹ is absent or C₁₋₄ linear or branched alkylidene;
X¹² is C₁₋₄ linear or branched alkylidene;
═is a saturated or unsaturated bond;

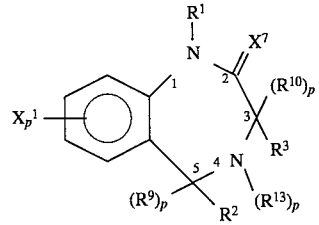

wherein R¹, R², R⁴, R⁵, R⁶, R⁸, R⁹, R¹⁰, R¹¹, R¹², R¹³, R¹⁴, R¹⁵, p, q, r, X¹, X², X³, X⁵, X⁶, X⁷, X⁸, X⁹, X¹⁰, X¹¹ and X¹² are as defined above, $$R^3 \text{ is } -X^{11}NR^{18}(CH_2)_qR^{16}, -X^{11}NR^{18}CX^{11}R^7,$$

$$-NH(CH_2)_{2-3}NHR^7, -NH(CH_2)_{2-3}NHCOR^7,$$

$$-X^{11}CX^9X^{11}R^7, -X^{11}X^9\underset{NHCOOR^{14}}{CCHCH_2R^7} -X^{11}NR^{18}CX_a^9X^{11}R^7,$$

-continued

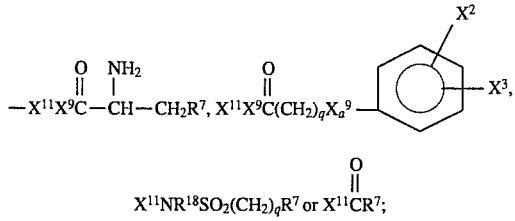

$$X^{11}NR^{18}SO_2(CH_2)_qR^7 \text{ or } X^{11}CR^7;$$

$R^7$ is α- or β-napthyl, substituted or unsubstituted phenyl (wherein the substituents may be 1 to 2 of halo, $-NO^2$, $-OH, -X^{11}NR^4R^5$, loweralkyl, $CF_3$, $CN$, $SCF_3$, $C=CH$, $CH_2SCF_3$,

$OCHF_2$, $SH$, $SPh$, $PO_3H$, loweralkoxy, loweralkylthio or $COOH$), 2-, 3-, 4-pyridyl

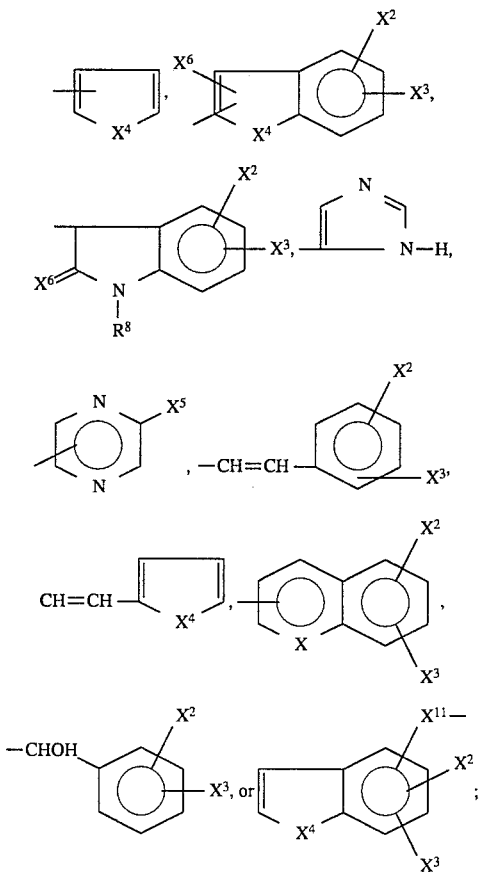

$R^{16}$ is alpha or beta naphthyl or 2-indolyl;
$R^{18}$ is H or loweralkyl; and
═is a saturated or unsaturated bond.

Preferred compounds for use in the pharmaceutical composition of the instant invention are: lorglumide which is DL-4-(3,4-dichlorobenzoyl-amino)-5-(dipentylamino)-5-oxopentanoic acid, loxiglumide which is (±)-4-[(3,4-dichlorobenzoyl)-amino]5-[(3-methoxypropyl)pentylamino]5-oxo-pentanoic acid, L-364718 which is 3(S)-(−)-N-(2,3-dihydro- 1-methyl-2-oxo-5-phenyl-1H-1,4-benzodiazepin-3-yl)- 1H-indole-2-carboxamide, and L-365,260 which is (R)-N-(2,3-dihydro-1-methyl-2-oxo-5-phenyl-1H- 1,4-benzodiazapine-3-yl)-N'-(3-methylphenyl)urea.

The instant invention also covers at least 0.05 mg/kg to about 50 mg/kg of a compound, as defined above, be present in the composition.

The instant invention also relates to a composition which is in oral dosage form.

The instant invention also relates to a method for treating psychoses, especially schizophrenia, in a mammal in need of such treatment which comprises administering a pharmaceutical composition of the instant invention in unit dosage form to said mammal.

The instant invention also relates to a method for treating anxiety in a mammal in need of such treatment which comprises administering a pharmaceutical composition of the instant invention in unit dosage form to said mammal.

The instant invention also relates to a method for treating the withdrawal response produced by chronic treatment followed by withdrawal of diazepam, nicotine, alcohol or cocaine.

The compounds used in the invention may contain asymmetric carbon atoms. The invention includes the use of diastereomers, mixtures of diastereomers, or the use of mixed or the individual optical enantiomers. The invention includes all such forms of the compounds.

The compounds used in the instant invention include solvates, hydrates and pharmaceutically acceptable salts thereof.

The pharmaceutically acceptable salts of the compounds used in the present invention include conventional non-toxic salts or quaternary ammonium salts.

The usefulness of the compounds of the instant invention as agents for treating psychoses and/or anxiety or withdrawal symptoms is demonstrated in the following pharmacological test procedure.

METHODS

The compounds of the instant invention are useful as anxiolytic agents as described and discussed below.

FIGS. 1A–1D illustrate the effectiveness of orally administered compound L-365260. Anxiolytic activity was assessed in the light/dark exploration test in the mouse (B. J. Jones, et al, *Br. J. Pharmacol.* 93:985–993, 1988).

Generally the number of mice used was 5 and the pretreatment time was about 40 minutes. The compound was given p.o. in 1- and 10-mg/kg doses.

The apparatus was an open-topped box, 45 cm long, 27 cm wide, and 27 cm high, divided into a small (⅖) area and a large (⅗) area by a partition that extended 20 cm above the walls. There was a 7.5×7.5 cm opening in the partition at floor level. The small compartment was painted black and the large compartment white. The floor of each compartment was marked into 9 cm squares. The white compartment was illuminated by a 100-watt tungsten bulb 17 cm above the box and the black compartment by a similarly placed 60-watt red bulb. The laboratory was illuminated with red light.

All tests were performed between 13 hundred hours, 0 minutes and 18 hundred hours, 0 minutes. Each mouse was tested by placing it in the center of the white area and allowing it to explore the novel environment for five minutes. Its behavior was recorded on videotape and the behavioral analysis was performed subsequently from the recording. Five parameters were measured: the latency to entry into the dark compartment, the time spent in each area, the number of transitions between compartments, the number of lines crossed in each compartment, and the number of rears in each compartment.

In this test an increase in the time spent in the white area is a sensitive measure of the anxiolytic effects of several standard anxiolytic drugs. Drugs were dissolved in water or saline and administered either subcutaneously, intraperitoneally, or by mouth (PO) via a stomach needle.

Drugs such as alcohol, cocaine, diazepam and nictoine can also be used in the light/dark exploration test in the mouse. For example, alcohol can be given in the drinking water as an 8% W/V solution for fourteen days. After a twenty-four hour withdrawal period the withdrawal response may be blocked by a composition of the instant invention when administered 10 mg/kg i.p. twice daily.

Figure 1C:
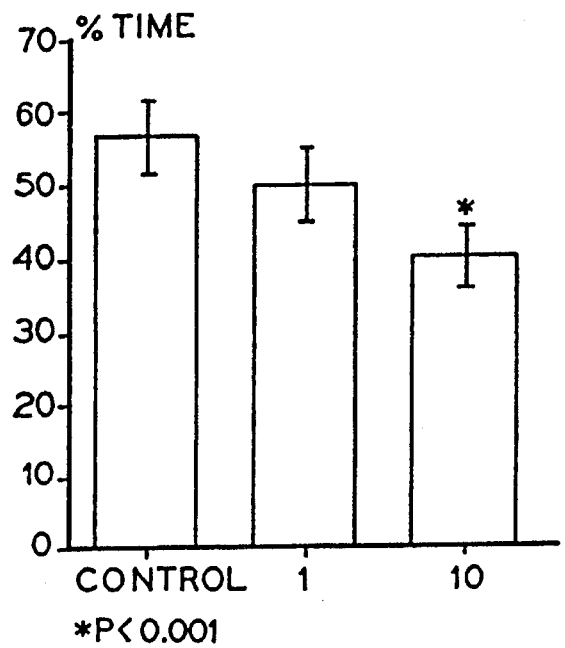
FIG. 1C. This figure depicts the relative time spent in the dark compartment of the box. The horizontal axis indicates the dosage of L-365,260 in mg/kg. The vertical axis indicates the percent of time spent in the dark portion of the box.
Figure 1D:
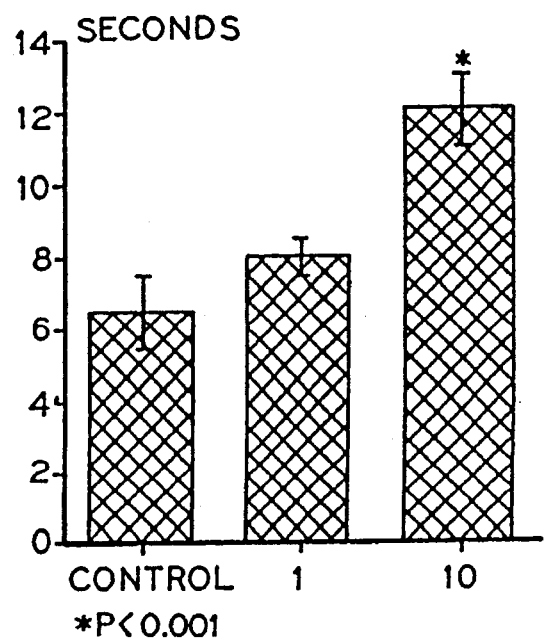
FIG. 1D. This figure depicts the latency period which was observed for the animals going from the light to the dark portion of the box. The horizontal axis shows the dosage of L-365,260 in mg/kg. The number of seconds required to make the light to dark transition is indicated on the vertical axis.

The results obtained with L-365,260 are shown in FIGS. 1A-1D. Control mice, not treated with L-365,260, but subjected to the aversive stimulus, showed a high level of rearing and line crossing activity in the black compartment compared to the white compartment. Treatment with L-365, 260 10 mg/kg orally reversed this response and the mice now showed higher rearing and line crossing activity in the white compartment than in the black compartment. FIGS. 1C-1D also show that L-365,260 reduced the total time spent by the mice in the black compartment and increased the time latency of the mice moving from the white side to the black side. These results show that L-365,260 possesses anxiolytic activity in this test.

The compositions of the instant invention are also useful as antipsychotic agents. The compounds of the instant composition were tested for their ability to reduce the effects of intra-accumbens amphetamine in the rat as described hereinafter.

Male Sprague Dawley (CD) Bradford strain rats were used. The rats were housed in groups of five at a temperature of 21°±2° C. on a 12 hour light-dark cycle of lights-on between 07 hours 00 minutes and 20 hours 00 minutes. Rats were fed CRM diet (Labsure) and allowed water ad libitum.

Rats were anesthetized with chloral hydrate (400 mg/kg$^{-1}$ SC) and placed in a Kopf stereotaxic frame. Chronically indwelling guide cannulae (constructed of stainless steel tubing 0.65 mm diameter held bilaterally in Parspex holders) were implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, Lat. ±4.5) (atlas of De Groot, 1959). The guides were kept patent during a 14-day recovery period using stainless steel stylets, 0.3 mm diameter, which extended 0.5 mm beyond the guide tips.

Rats were manually restrained and the stylets removed. Intracerebral injection cannulae, 0.3 mm diameter, were inserted and drugs delivered in a volume of 0.5 μl over 5 seconds (a further 55 seconds was allowed for deposition) from Hamilton syringes attached via polythene tubing to the injection units. Animals were used on a single occasion only.

Behavioral experiments were conducted between 07 hours 30 minutes and 21 hours 30 minutes in a quiet room maintained at 22°±2° C. Rats were taken from the holding room and allowed one hour to adapt to the new environment. Locomotor activity was assessed in individual screened Perspex cages (25×15×15 cm (high)) (banked in groups of 30) each fitted with one photocell unit along the longer axis 3.5 cm from the side; this position has been found to minimize spurious activity counts due to, for example, preening and head movements when the animal is stationary. Interruptions of the light beam were recorded every 5 minutes. At this time animals were also observed for the presence of any nonspecific change in locomotor activity, e.g., sedation, prostration, stereotyped movements, that could interfere with the recording of locomotor activity.

The abilities of the compounds to inhibit the hyperactivity caused by the injection of amphetamine into the nucleus accumbens of the rat was measured.

An increase in locomotor activity followed the bilateral injection of amphetamine (20 μg) into the nucleus accumbens; peak hyperactivity (50 to 60 counts 5 minutes$^{-1}$) occurred 20 to 40 minutes after injection.

Intraperitoneal injection of the rats with compounds of this invention reduces the hyperactivity caused by the intra-accumbens injection of amphetamine. This test is known to be predictive of antipsychotic activity (Costall, Domeney & Naylor & Tyers, *Brit 5 Pharmac.* 92:881–894).

For preparing pharmaceutical compositions from compounds, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is fist melted and the active ingredient is dispersed therein by, for example, stirring. The molten homogeneous mixture is then poured into convenient sized molds and allowed to cool and solidify.

The powders and tablets preferably contain 5 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspension, and emulsions. Sterile water or water-propylene glycol solutions of the active compounds may be mentioned as an example of liquid preparations suitable for parenteral administration. Liquid preparations can also be formulated in solution in aqueous polyethylene glycol solutions.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

When a compound of formula I, IA, II, or III is used in the instant invention in a human subject, the daily dosage will normally be determined by the prescribing physician with the dosage generally varying according to the age, weight, and response of the individual patient, as well as the severity of that patient's symptoms. However, in most instances, an effective daily dosage will be in the range of from about 0.05 mg/kg to about 50 mg/kg of body weight, and preferably, of from 0.5 mg/kg to about 20 mg/kg of body weight, administered in single or divided doses. In some cases, however, it may be necessary to use dosages outside these limits.

Examples of formulations of compounds or salts thereof of the instant invention are:

EXAMPLE 1

Injectables

Lorglumide with water for injection USP q.s.

The hydrochloride salt of the compound is dissolved in water and passed through a 0.2-micron filter. Aliquots of the filtered solution are added to ampoules or vials, sealed and sterilized.

EXAMPLE 2

| Syrups 200 mg/5 ml syrup | |
|---|---|
| Compound | 12.5 g |
| Purified Water USP | 200 ml |
| Cherry Syrup qu | 1000 ml |

The compound is dissolved in water and to the resulting solution the syrup is added with mild stirring.

EXAMPLE 3

| Capsules 50 mg, 100 mg, or 200 mg | |
|---|---|
| Compound 1 | 250 g |
| Lactose USP, Anhydrous q.s. or | 250 g |
| Sterotex Powder HM | 5 g |

Combine the compound and the lactose in a tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. The appropriate sized capsules are filled with 141 mg, 352.5 mg, or 705 mg of the blend, respectively, for the 50 mg, 125 mg, and 250 mg containing capsules.

EXAMPLE 4

| Tablets 50 mg, 100 mg, or 200 mg | |
|---|---|
| Corn Starch NF | 200 g |
| Cellulose, Microcrystalline | 46 g |
| Sterotex Powder HM | 4 g |
| Purified Water q.s. or | 300 ml |

Combine the corn starch, the cellulose, and Compound 1 together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for five minutes by drum rolling. Compressed tablets of 150 mg, 375 mg, and 750 mg, respectively, of the total mix are formed with appropriate sized punches the 50 mg, 125 mg, or 500 mg containing tablets.

We claim:

1. A method for treating or preventing the withdrawal response produced by withdrawal of chronic treatment with diazepam in a mammal in need of such treatment which comprises administering a pharmaceutical composition in unit dosage form of at least one of the following CCK-ligands:

pharmaceutically active derivatives of D,L-glutamic acid and D,L-aspartic acid of formula:

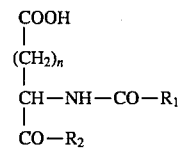

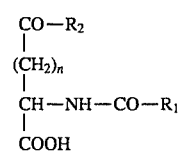

wherein n is 1 or 2;

$R_1$ is a phenyl group mono-, di, or tri-substituted with linear or branched $C_1$-$C_4$ alkyl groups, which may be the same or different, or with halogens, with a cyano group or with a trifluoromethyl group; and $R_2$ is selected from the group consisting of morpholino, piperidino and amino which amino can have one or two linear, branched or cyclic alkyl group substituents which substituents contain from 1 to 8 carbon atoms and which substituents may be the same or different.

2. A method for treating or preventing the withdrawal response produced by withdrawal of chronic use of cocaine in a mammal in need of such treatment which comprises administering a pharmaceutical composition in unit dosage form of at least one of the following CCK-ligands:

pharmaceutically active derivatives of D,L-glutamic acid and D,L-aspartic acid of formula:

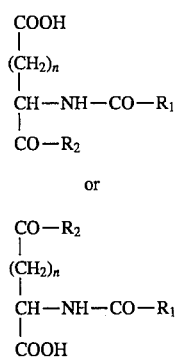

wherein n is 1 or 2;

$R_1$ is a phenyl group mono-, di, or tri-substituted with linear or branched $C_1$-$C_4$ alkyl groups, which may be the same or different, or with halogens, with a cyano group or with a trifluoromethyl group; and $R_2$ is selected from the group consisting of morpholino, piperidino and amino which amino can have one or two linear, branched or cyclic alkyl group substituents which substituents contain from 1 to 8 carbon atoms and which substituents may be the same or different.

3. A method for treating or preventing the withdrawal response produced by withdrawal of chronic use of alcohol in a mammal in need of such treatment which comprises administering a pharmaceutical composition in unit dosage form of at least one of the following CCK-ligands:

pharmaceutically active derivatives of D,L-glutamic acid and D,L-aspartic acid of formula:

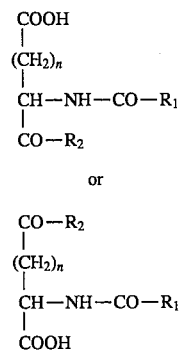

wherein n is 1 or 2;

$R_1$ is a phenyl group mono-, di-, or tri-substituted with linear or branched $C_1$-$C_4$ alkyl groups, which may be the same or different, or with halogens, with a cyano group or with a trifluoromethyl group; and $R_2$ is selected from the group consisting of morpholino, piperidino and amino which amino can have one or two linear, branched or cyclic alkyl group substituents which substituents contain from 1 to 8 carbon atoms and which substituents may be the same or different.

4. A method for treating or preventing the withdrawal response produced by withdrawal of chronic use of nicotine in a mammal in need of such treatment which comprises administering a pharmaceutical composition in unit dosage form of at least one of the following CCK-ligands:

pharmaceutically active derivatives of D,L-glutamic acid and D,L-aspartic acid of formula:

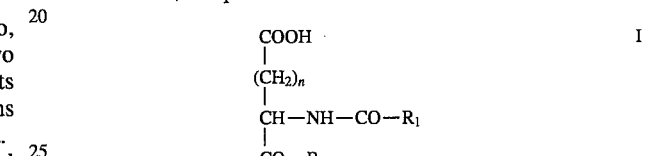

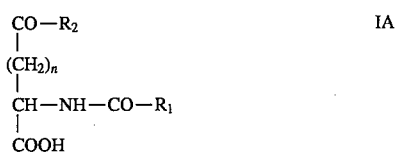

wherein n is 1 or 2;

$R_1$ is a phenyl group mono-, di, or tri-substituted with linear or branched $C_1$-$C_4$ alkyl groups, which may be the same or different, or with halogens, with a cyano group or with a trifluoromethyl group; and $R_2$ is selected from the group consisting of morpholino, piperidino and amino which amino can have one or two linear, branched or cyclic alkyl group substituents which substituents contain from 1 to 8 carbon atoms and which substituents may be the same or different.

* * * * *